US010506813B2

(12) United States Patent
Riggs et al.

(10) Patent No.: US 10,506,813 B2
(45) Date of Patent: Dec. 17, 2019

(54) COMPOSITIONS AND METHODS FOR CONTROLLING PLANT-PARASITE NEMATODE

(71) Applicant: BASF CORPORATION, Florham Park, NJ (US)

(72) Inventors: Jennifer Lynn Riggs, Raleigh, NC (US); Eder Leonardo Sastoque Cala, Opelika, AL (US); Joseph W. Kloepper, Auburn, AL (US); Katheryn Kay Scott Lawrence, Auburn, AL (US); Juan David Castillo Russi, Auburn, AL (US)

(73) Assignee: BASF CORPORATION, Florham Park, NJ (US)

(*) Notice: Subject to any disclaimer, the term of this patent is extended or adjusted under 35 U.S.C. 154(b) by 0 days.

(21) Appl. No.: 15/405,074

(22) Filed: Jan. 12, 2017

(65) Prior Publication Data
US 2017/0188586 A1 Jul. 6, 2017

Related U.S. Application Data

(63) Continuation of application No. 14/426,806, filed as application No. PCT/US2013/058866 on Sep. 10, 2013, now abandoned.

(60) Provisional application No. 61/700,054, filed on Sep. 12, 2012.

(51) Int. Cl.
*A01N 63/02* (2006.01)
*C12N 9/20* (2006.01)
*C12N 9/28* (2006.01)
*C12N 9/42* (2006.01)
*C12N 9/52* (2006.01)
*C12N 9/26* (2006.01)
*C12N 9/48* (2006.01)

(52) U.S. Cl.
CPC ........... *A01N 63/02* (2013.01); *C12N 9/20* (2013.01); *C12N 9/2414* (2013.01); *C12N 9/2417* (2013.01); *C12N 9/2437* (2013.01); *C12N 9/48* (2013.01); *C12N 9/52* (2013.01); *C12Y 301/01003* (2013.01); *C12Y 302/01001* (2013.01); *C12Y 302/01004* (2013.01); *C12Y 304/00* (2013.01)

(58) Field of Classification Search
CPC .... A01N 63/00; A01N 51/00; A01N 2300/00; A01N 43/40; A01N 25/00; A01N 43/36; A01N 43/88; A01N 47/38; A01N 47/40; A01N 47/14; A01N 63/02; A01N 43/50; A01N 47/06; A01N 47/44; A01N 63/04; A01N 47/08; A01N 47/24; A01N 37/46; A01N 47/34; A01N 25/24; A01N 65/20; A01N 53/00; C12N 15/8275; C12N 15/8286; C12N 9/20; C12N 9/2414; C12N 9/2417; C12N 9/2437; C12N 9/48; C12N 9/52; C12N 1/20; C12N 15/67; C12N 15/75; C12N 9/2482; C12N 9/248; C12R 1/07; Y02A 40/162; Y02A 50/356; C12Y 301/01003; C12Y 302/01001; C12Y 302/01004; C12Y 304/00; C12Y 302/01008; C12Y 304/21062; C05F 11/08; C05F 11/10; A01C 1/08; C11D 3/38645; C12P 21/02; C12P 19/04; Y02E 50/343; Y02W 30/47; C05G 3/02; C07K 1/30; C07K 1/36; C07K 7/00; C07K 7/64
See application file for complete search history.

(56) References Cited

U.S. PATENT DOCUMENTS

| | | | |
|---|---|---|---|
| 5,958,728 A * | 9/1999 | Sloma | C12N 15/75 435/252.31 |
| 9,000,138 B2 * | 4/2015 | Schnorr | C11D 3/38645 435/252.3 |
| 2011/0200571 A1 * | 8/2011 | Bell | A01C 1/08 424/93.46 |
| 2014/0056866 A1 * | 2/2014 | Andersch | A01N 43/40 424/93.461 |
| 2014/0179588 A1 * | 6/2014 | Schnorr | C12N 9/2437 510/392 |

OTHER PUBLICATIONS

PeerReview 2012, EFSA J. 10(10):2868. 2012.*
Mendoza et al website for book. 2008.*
Park et al 2004 "Production of . . ."pp. 271-276. 2004.*
Shen et al, "Aggregation of the Naturally Occurring Lipopeptide, Surfactin, at Interfaces and in Solution: An Unusual Type of Surfactant?", American Chemical Soc., Langmuir 2009, Vo. 25, pp. 4211-4218.*
BPDB: Bio-Pesticides DataBase, University of Hertfordshire, https://sitem.herts.ac.uk/aeru/bpdb/Reports/1700.htm. Last updated : Sunday May 27, 2018. Contact: aeru@herts.ac.uk.*
Russi, Juan D.C., "Biocontrol Studies of Rotylenchulus reniformis in Cotton Crops in Alabama", Auburn University, pp. 1-154, Aug. 2012.*
Rehman et al, "Identification and Characterization of the Most Abundant Cellulases in Stylet Secretions from Globodera rostochiensis" Phytopathology pp. 194-202, 2009.*
Cai-Yi Wen et al , "Purification and Structural Analysis of Surfactin Produced by Endophytic Bacillus subtilis EBS05 and its Antagonistic Activity Against Rhizoctonia cerealis", Plant Pathol. J. 27(4): 342-348, 2011.*

(Continued)

Primary Examiner — Deborah K Ware
(74) Attorney, Agent, or Firm — McBee Moore Woodward & Vanik IP, LLC

(57) ABSTRACT

An composition having anti-nematodal activity derived from *Bacillus firmus* bacteria selected from the group consisting of isolated biosurfactant, isolated protease enzyme, isolated amylase, isolated lipase, and isolated cellulase, is disclosed. The disclosure also provides for methods of making the same, methods of controlling plant-parasite nematode, and methods of protecting plants.

18 Claims, 6 Drawing Sheets

(56) References Cited

OTHER PUBLICATIONS

Stewart, "Nematode Management in Cotton", UTcrops News Blog, pp. 1-3, Mar. 31, 2011.*
International Search Report from corresponding PCT/US2013/058866, dated Oct. 24, 2013.
Castillo, "Biocontrol Studies of Rotylenchulus reniformis in Cotton Crops in Alabama", Aug. 4, 2012, pp. 1-154, XP055084212.

\* cited by examiner

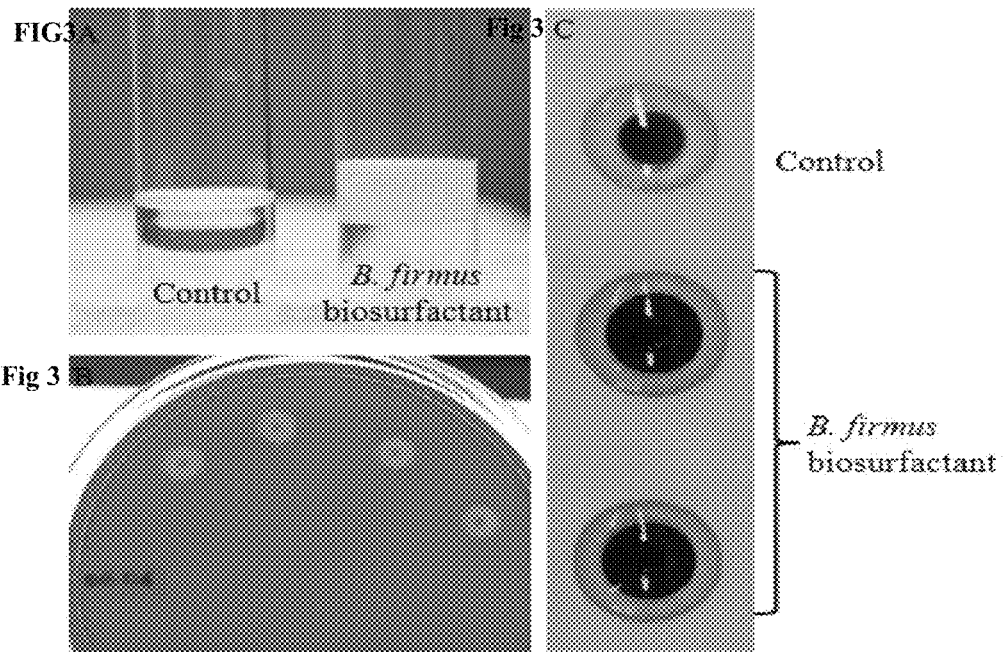
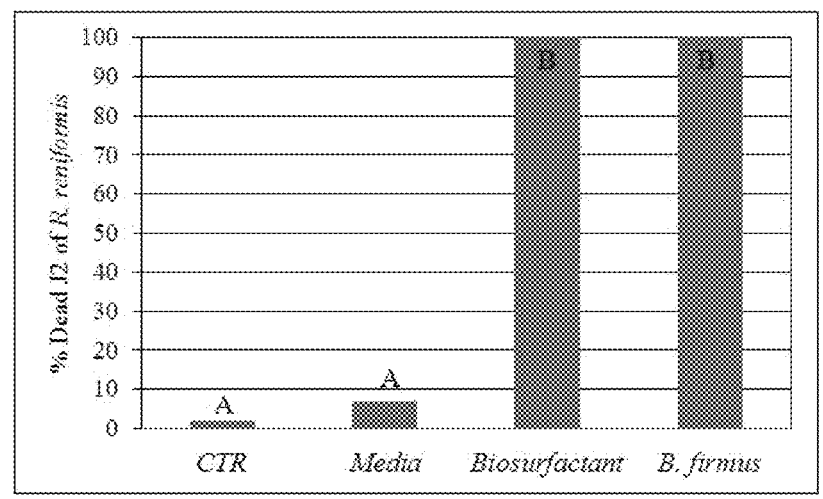
Fig. 4

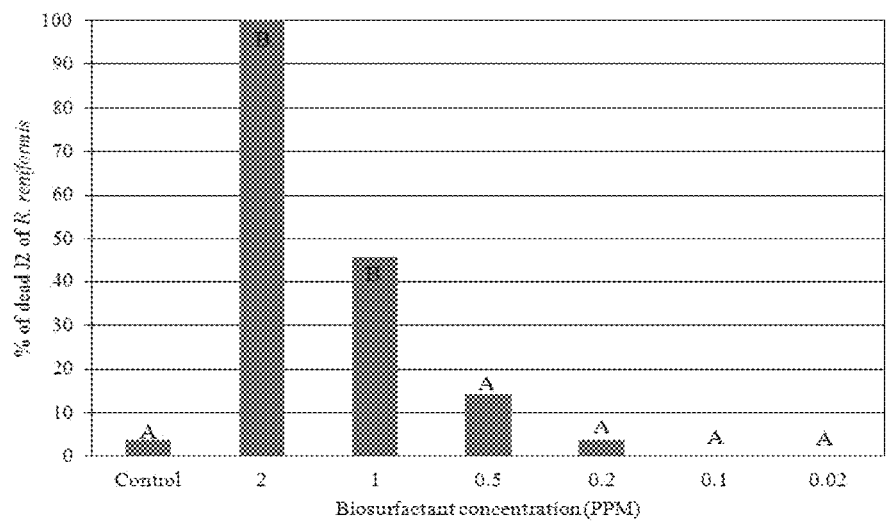
Fig. 5
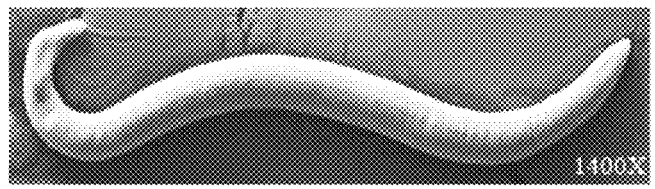
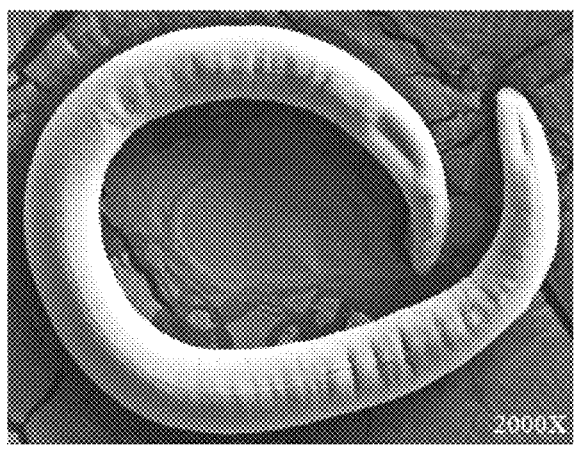

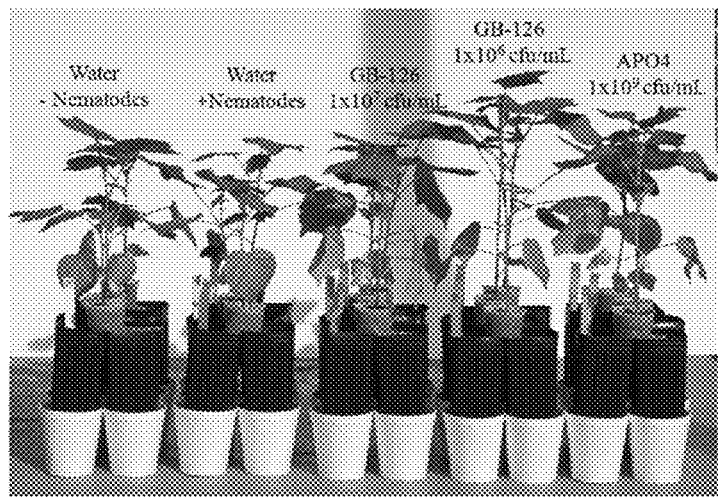
Fig. 7
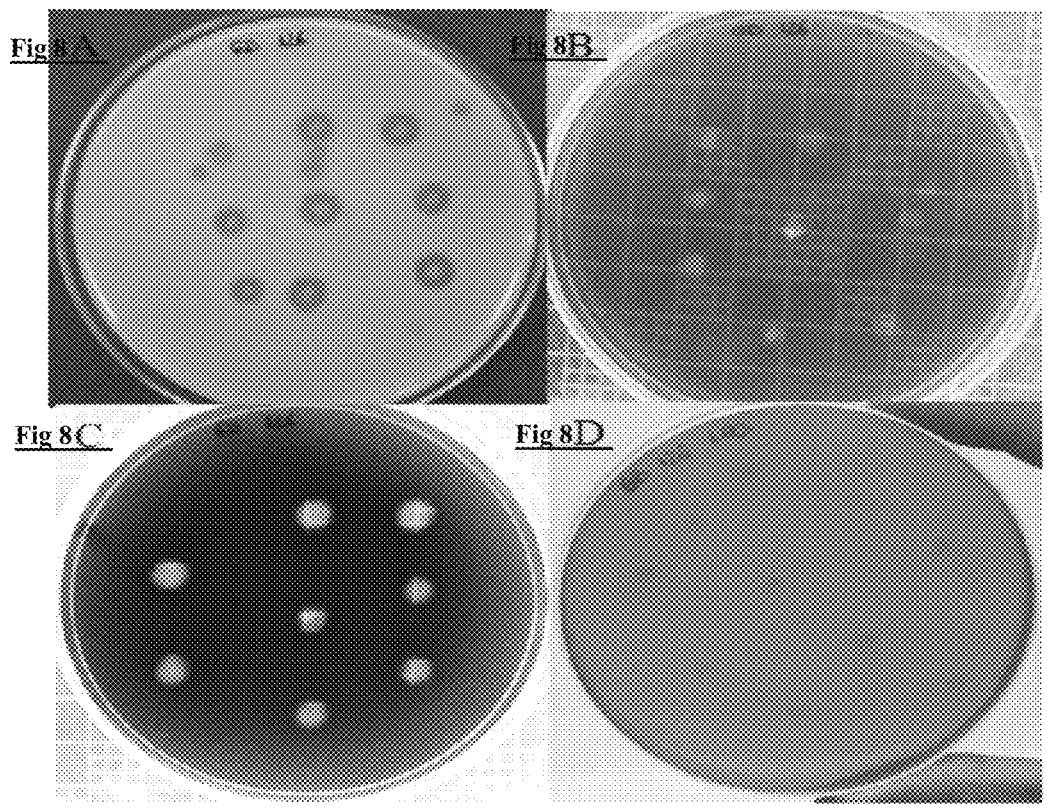

COMPOSITIONS AND METHODS FOR CONTROLLING PLANT-PARASITE NEMATODE

CROSS REFERENCE TO RELATED APPLICATIONS

This application is a Continuation of U.S. application Ser. No. 14/426,806, filed Mar. 9, 2015, which is a § 371 National Stage Application of PCT/US2013/058866, filed Sep. 10, 2013, and claims priority to U.S. 61/700,054, filed Sep. 12, 2012.

An entity having anti-nematodal activity derived from *Bacillus firmus* bacteria selected from the group consisting of isolated biosurfactant, isolated protease enzyme, isolated amylase, isolated lipase, and isolated cellulase, is disclosed. The disclosure also provides for compositions comprising the same, methods of making the same, methods of controlling plant-parasite nematode, and methods of protecting plants.

BACKGROUND

Bacteria are an important group of natural antagonists of plant-parasitic nematodes. Bacteria are distributed broadly, have diverse modes of action, and have broad host ranges (Tian, B. et al.). They exhibit diverse modes of action against nematodes that include parasitism, production of toxins, antibiotics, or lytic enzymes; induce systemic resistance, and promote plant health (Aatlen, P. M. et al.; Kerry, B. R. 2000; Kerry, B. R. 1987; Siddiqui, Z. A. et al.; Stirling, G. R. 1991; Tian, B. et al.; Van Loon, L. C. et al.). Furthermore, bacteria can be in direct contact with the entrance sites of the nematodes and influence root exudates that can affect the nematode development (Sikora, R. A. 1992). The genera *Pasteuria, Pseudomonas*, and *Bacillus* have shown promising potential for nematode biocontrol (Meyer S. L. F; Siddiqui, Z. A. et al.; Stirling, G. R.; Tian, B. et al.).

*Bacillus firmus* strain GB-126 is a nematode biocontrol agent registered initially in a bionematicide in Israel under the trade name of BIONEM® WP (Blachinsky, D. et al.; Keren-Zur et al.). This formulation was shown to reduce galling index caused by *Meloidogyne* spp. on cucumber and tomato plots (Keren-Zur et al.). Also, under field conditions, suppression of *Meloidogyne* spp. was observed within 2 months of transplanting cucumbers and continued through the end of the experiments (Giannakou, O. I. et al., 2004). Control provided by *B. firmus* GB-126 was less effective than the soil fumigant dazomet. However, its combination with soil solarization improves nematode control giving results similar to dazomet use (Giannakou, O. I. et al. 2007). Furthermore, when *B. firmus* GB-126 was evaluated in tomato seedlings in the greenhouse, it reduced gall formation by 91%, final nematode population by 76%, and the number of *M. incognita* eggs by 45% (Terefe, M. et al.).

In other study, a formulation of *B. firmus* that contains seaweed extract (BIONEM® L) was able to reduce *Helicotylenchus* spp. and *Tylenchorhynchus* spp. in golf greens (Wick, R. L. 2006). Furthermore, synergism of *B. firmus* with other nematode biocontrol agents has been reported to improve nematode reduction (Mendoza, A. R. et al. 2009). In banana, *B. firmus* was evaluated against *R. similis* and applied in combination with *F. oxysporum* and *P. lilacinus*, which reduced the infection of this migratory endoparasitic nematode (Mendoza, A. R. et al. 2009). Under in vitro conditions *B. firmus* was evaluated against the plant parasitic nematodes *Radopholus similis, Meloidogyne incognita*, and *Ditylenchus dipsaci. Bacillus firmus* produced bioactive secondary metabolites that were toxic to these nematode juveniles and reduced egg hatching (Mendoza, A. R. et al. 2008).

Thus, previous studies have demonstrated the antagonistic effect of bioactive secondary metabolites of *Bacillus firmus* GB-126 against plant parasitic nematodes. Nevertheless, the types of secondary metabolites and enzymatic properties involved and the role of possible induction of plant resistance have not been evaluated. Fewer and fewer traditional nematicide are available today and many that are available are very expensive or not environmentally and user friendly. Identification of a biological means to protection plants from pathogenic nematodes fits well into today's integrated pest management platform for agriculture. Understanding the single or multiple modes of actions of a biocontrol microbe can assist in the optimization of the growth of the microbe prior to formulating into a commercial product. Studies that evaluate the purpose of the various secondary metabolites can define which of the many metabolites should be optimized during the growth of the microbe. There are means available to optimize the growth media of the microbe to enhance production of one metabolite or another.

An object of the present invention is to provide a novel entity having anti-nematodal activity derived from *Bacillus firmus* bacteria selected from the group consisting of isolated biosurfactant, isolated protease, isolated amylase, isolated lipase, and isolated cellulase, is disclosed. Another object is to provide for compositions comprising the same. Another object is to provide for methods of making the same.

A further object is to provide for methods of controlling plant-parasite nematode, and methods of protecting plants.

SUMMARY

In an aspect, the disclosure provides for an a novel entity having anti-nematodal activity derived from *Bacillus firmus* bacteria selected from the group consisting of isolated biosurfactant, isolated protease, isolated amylase, isolated lipase, and isolated cellulose.

In an aspect, the disclosure provides for a novel composition having anti-nematodal activity comprising at least one entity derived from *Bacillus firmus* bacteria selected from the group consisting of an isolated biosurfactant, an isolated protease, an isolated amylase, an isolated lipase, and an isolated cellulase.

In an aspect, the disclosure provides for an extract of a *Bacillus firmus* culture having the following characteristics: anti-nematodal activity and presence of a biosurfactant.

In an aspect, the disclosure provides for an extract of a *Bacillus firmus* culture having the following characteristics: anti-nematodal activity and activity selected from the group consisting of protease activity, amylase activity, lipase activity, and cellulase activity.

In an aspect, the disclosure also provides for a method of making the same.

The disclosure also provides for a method of controlling plant-parasitic nematode by applying an entity or composition as described herein to to a plant, the seed material, or the area on which the plant grows. In an aspect, the disclosure provides for a method of protecting a plant by applying an entity or composition as described herein to a plant, the seed material, or the area on which the plant grows.

In an aspect, the plant-parasitic nematode is *Rotlyenchulus reniformis*.

BRIEF DESCRIPTION OF THE FIGURES

FIG. 3 sets forth tests of biosurfactant production of *B. firmus* GB-126. (A) represents the positive emulsification of kerosene. (B) represents halo formation due to cell lysis in blood agar. (C) represents positive oil drop collapse test.

FIG. 4 sets forth the effect of biosurfactant produced by *B. firmus* on *R. reniformis* second stage juveniles after 30 minutes of inoculation ($P \leq 0.05$) as compared to BP media and water controls and *B. firmus* bacteria.

FIG. 5 sets forth the effect of purified biosurfactant produced by *B. firmus* at different concentrations (ppm) on *R. reniformis* second stage juveniles after 30 minutes of inoculation under in vitro conditions ($P \leq 0.05$).

FIG. 6 sets forth the photos of second stage juveniles of *R. reniformis* form (control and after application of 2 ppm *B. firmus* biosurfactant) observed under SEM in in vitro trial.

FIG. 7 sets forth photos of growth of cotton plants after systemic resistance trial of *B. firmus* GM-126 and *S. marcescens* against *R. reniformis* in cotton plants.

FIG. 8 sets forth the enzyme reaction test of *B. firmus* GB-126: (A) represents production of proteases, (B) represents production of amylases, (C) represents production of cellulases, and (D) represents production of chitinases.

DETAILED DESCRIPTION

Figure 1:
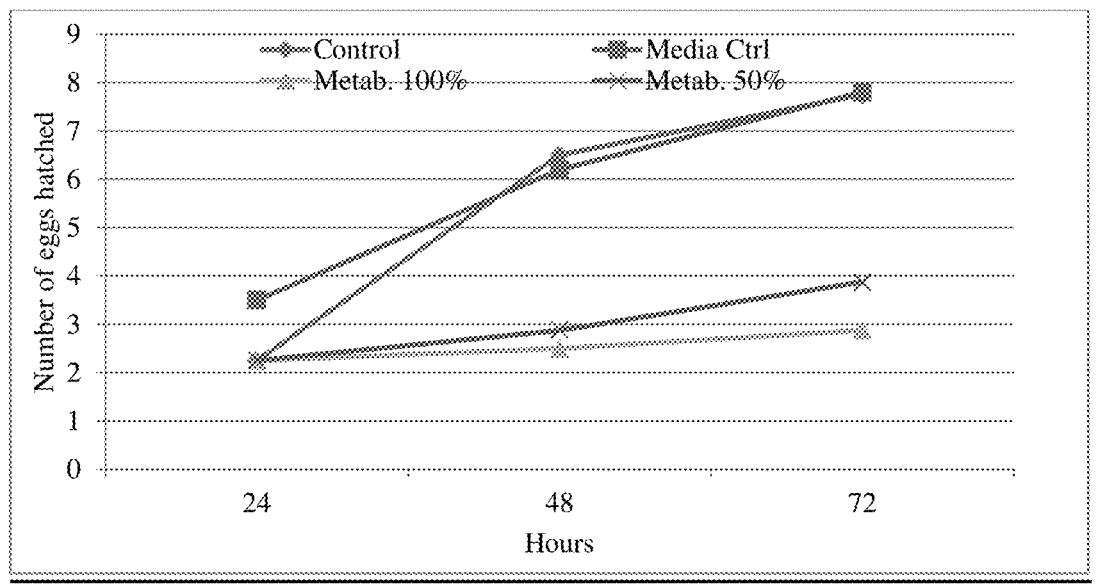
FIG. 1 sets forth the effects of *B. firmus* metabolites at 100% and 50% concentration on *R. reniformis* eggs as compared to water and media control.

In an aspect, the disclosure provides for an a novel entity having anti-nematodal activity derived from *Bacillus firmus* bacteria selected from the group consisting of isolated biosurfactant, isolated protease, isolated amylase, isolated lipase, and isolated cellulase.

Anti-nematodal activity is understood as meaning any activity useful in controlling or killing nematodes, such as reducing nematode egg hatching or paralyzing juveniles of nematodes. Testing for anti-nematodal activity is done both in-vitro and in-vivo through laboratory and greenhouse procedures. In-vitro testing can involve testing eggs and/or juvenile nematodes in selective media in small 96-well plates and measurements done by microspopic evaluations. Proper control treatments would be combined to monitor and compare activity. Under greenhouse studoes soil was autoclaved using two 90 minute cycles at 130° C. at 1.0 kg/cm³ pressure with a 24 hour cool down between cycles to remove any natural competition for the microflora. The vermiform stages were extracted from the soil by the modified gravity screening and sucrose centrifugation-flotation. Eggs stages were extracted from cotton roots by shaking the root system in a 1% NaOCl solution for four minutes at 120 rpm. The nematode suspension was collected and rinsed with water through a 25 μm sieve. Females in roots were stained with acid fuschin to facilitate enumeration of the females invading the root. Variables measured included plant height, shoot and root weights, females and eggs per gram of root, and the number of vermiform life stages in soil.

In an aspect, the strain of *Bacillus firmus* is GB-126. In an aspect, the entity described herein has anti-nematodal activity against Reniform nematode, *Rotlyenchulus* spp.; Dagger nematode, *Xiphinema* spp.; Lance nematode, *Hoplolaimus* spp.; Pin nematode, *Paratylenchus* spp.; Ring nematode, *Criconemoides* spp.; Rootknot nematode, *Meloidogyne* spp.; Sheath nematode, *Hemicycliophora* spp.; Spiral nematode, *Helicotylenchus* spp.; Stubbyroot nematode, *Trichodorus* spp.; Cyst nematode, *Heterodera* spp.; Sting nematode, *Belonolaimus*, spp.; and/or Stunt nematode, *Tylenchorhynchus* spp.

In an aspect, the entity as described herein is a biosurfactant obtainable by a method comprising: obtaining a medium in which *Bacillus firmus* bacteria has been grown and precipitating the biosurfactant from the medium.

Biosurfactant is understood to mean microbially produced surface-active compounds. They are amphiphilic molecules with both hydrophilic and hydrophobic regions causing them to aggregate at the interfaces between fluids with different polarities such as water and hydrocarbons (Jennings E. R. et al., 2000).

Multiple initial tests were conducted to determine the production of biosurfactant from *B. firmus*. The bacterium was grown under blood agar, where a positive production of biosurfactant is indicated by a transparent halo around the bacterial colony. Additional testing, *B. firmus* was cultured on nutrient broth at 30° C. for 24 hours. Subsequently, the living cells were recovered by centrifugation at 5,181×g for 15 minutes, and cells were washed twice with NaCl 0.85% (w/v) and later suspended in 5 ml of NaCl 0.85% (w/v). They were used to inoculate 45 ml of saline Davis minimal broth with an inoculum ratio of 1% (v/v). The composition was $K_2HPO_4$ 5.23 g/l, $KH_2PO_4$ 1.91 g/l, $MgSO_4$ 0.09 g/l, $(NH_4)_2SO_4$ 1 g/l, as well as 1 ml/l of trace elements solution ($CoCl_3$ 20 mg/l, $H_3BO_3$ 30 mg/l, $ZnSO_4$ 10 mg/l, $Cu_2SO_4$ 1 mg/l, $Na_2MoO_4$ 3 mg/l, $FeSO_4$ 10 mg/l and $MgSO_4$ 2.6 mg/l). Cultures were incubated at 30° C.±2 at 150 rpm for 3 days. Again *B. firmus* living cells were separated from the supernatant by centrifugation (20 minutes at 4000 xg). The supernatant was filtered through a Millipore filter 0.45-0.22 μm to obtain the final bacterial biosurfactant product. This final product was autoclaved twice for 30 minutes at 120° C. at 1 kg/cm³ pressure to kill all the bacterium's living cells and inactivate its enzymes. emulsifying activity of the cell-free supernatant was evaluated by mixing 0.5 ml with 0.5 ml of kerosene and 4 ml of distilled water to a disposable culture tube (borosilicate glass 16×150 mm). The negative control consisted of distilled water and kerosene, and the positive control consisted of distilled water, kerosene, and Triton X-100 (100 mg/ml). Each tube was agitated in a vortex for 1 min and was left to stand for 24 hours. The height of the emulsification ring was then measured in millimeters and compared to that of the chemical emulsifier. If there was positive production of surfactant, the kerosene emulsified it and produced foam. The third test consisted of an oil drop collapse in which one drop of the supernatant was placed on parafilm paper and a drop of oil was placed on top of it. If the drop of oil increased its diameter compared to the media control, the bacteria was considered to have produced a biosurfactant. Finally, the biosurfactant product was again tested under in vitro conditions in 96 well-plate against second stage juveniles of *R. reniformis*. Volumes of 100 μL of the treatments we transferred to each well, which contained approximately 16 juveniles of *R. reniformis*. Treatments for this trial were i) water control, ii) BPM control, iii) biosurfactant 100%, and iv) *B. firmus* 15×$10^7$ cfu/ml. Each treatment was replicated 8 times, and the entire trial was repeated twice. The number of juveniles paralyzed or dead was recorded 30 minutes after inoculation. Data were analyzed on SAS 9.1 (SAS Institute Inc.).

In an aspect, the medium in which *Bacillus firmus* bacteria has been grown is obtained by growing *B. firmus* bacteria aerobically in medium. There are numerous mediums in which the bacteria can grow on, for example, a minimal salt medium supplemented with yeast extract and glucose. In an aspect, for biosurfactant isolation, bacterial cells are removed from the surfactant-containing medium by centrifugation, and the biosurfactant is precipitated from the supernatant by adding an acid. The acid precipitates are recovered by centrifugation and are extracted with a solvent. After precipitation with an acid, the crude fraction dissolved in the solvent is evaporated, and the final purified biosurfactant product is diluted in distilled water at specific concentrations.

In an aspect, the entity as described herein is an isolated protease. Protease is understood to mean any polypeptides or complex of polypeptides or fragments of polypeptides having protease activity. Production of protease enzymes were evaluated by use of milk agar assay. A clear halo following 24 hr period of incubation is recorded as a positive indication for the production of proteases.

In an aspect, the entity as described herein is an isolated amylase. Amylase is understood to mean any polypeptides or complex of polypeptides or fragments of polypeptides having amylase activity. Production of amylase enzymes were evaluated by use of starch agar assay. A clear halo following 24 hr period of incubation is recorded as a positive indication for the production of amylases.

In an aspect, the entity as described herein is an isolated lipase. Lipase is understood to mean any polypeptides or complex of polypeptides or fragments of polypeptides having lipase activity. Production of lipase enzymes were evaluated by use of trybutirin agar assay. A clear halo following 24 hr period of incubation is recorded as a positive indication for the production of lipases.

In an aspect, the entity as described herein is an isolated cellulase. Cellulase is understood to mean any polypeptides or complex of polypeptides or fragments of polypeptides having cellulase activity. Production of cellulase enzymes were evaluated by use of carboximetil cellulose (CMC) agar agar assay. A clear halo following 24 hr period of incubation is recorded as a positive indication for the production of cellulases.

In an aspect, the disclosure provides for a novel composition having anti-nematodal activity comprising at least one entity derived from *Bacillus firmus* bacteria selected from the group consisting of an isolated biosurfactant, an isolated protease, an isolated amylase, an isolated lipase, and an isolated cellulase.

In an aspect, the strain of *Bacillus firmus* is GB-126. In an aspect, the composition described herein has anti-nematodal activity against *Rotlyenchulus reniformis*.

In an aspect, the composition described herein comprises an acid precipitate from a culture medium in which the *Bacillus firmus* bacteria was grown. In an aspect, the acid precipitate described herein is obtainable by a method comprising: adding an acid to a medium in which a *Bacillus firmus* bacteria has been grown to generate an acid precipitate, and (b) isolating the acid precipitate from the medium. In another aspect, the acid precipitate has anti-nemadodal activity.

In an aspect, the medium in which *Bacillus firmus* bacteria has been grown is obtained by growing *B. firmus* bacteria aerobically in medium. There are numerous mediums in which the bacteria can grow on, for example, a minimal salt medium supplemented with yeast extract and glucose. In an aspect, for biosurfactant isolation, bacterial cells are removed from the surfactant-containing medium by centrifugation, and the biosurfactant is precipitated from the supernatant by adding an acid. The acid precipitates are recovered by centrifugation and are extracted with a solvent. After precipitation with an acid, the crude fraction dissolved in the solvent is evaporated, and the final purified biosurfactant product is diluted in distilled water at specific concentrations.

In an aspect, the composition as described herein comprises of an isolated biosurfactant. In an aspect, the isolated biosurfactant concentration in the composition as described herein is greater than 0.5 ppm. In an aspect, the isolated biosurfactant concentration in the composition described herein is at least 1 ppm. In an aspect, the isolated biosurfactant concentration in the composition described herein is from 1 to 2 ppm. In an aspect the isolated biosurfactant concentration in the composition described herein is at least 2 ppm. In an aspect, the isolated biosurfactant concentration in the composition described herein is from 1 to 5 ppm. In an aspect, the isolated biosurfactant concentration in the composition described herein is from 2 to 5 ppm.

In an aspect, the composition as described herein is an isolated protease.

In an aspect, the composition as described herein is an isolated amylase.

In an aspect, the composition as described herein is an isolated lipase.

In an aspect, the composition as described herein is an isolated cellulase.

In an aspect, the disclosure provides for an extract of a *Bacillus firmus* bacteria having the following characteristics: anti-nematodal activity and presence of a biosurfactant.

In an aspect, the disclosure provides for an extract of a *Bacillus firmus* bacteria having the following characteristics: anti-nematodal activity and activity selected from the group consisting of protease activity, amylase activity, lipase activity, and cellulase activity.

Extract shall refer to any fraction extracted from reference material.

The disclosure also provides for a method of controlling plant-parasitic nematode by applying an entity or composition as described herein to a plant, the seed material (e.g. grains, seeds or vegetative propagation organs such as tubers or shoot parts with buds) or the area on which the plants grow (e.g. the area under cultivation).

In an aspect, the disclosure provides for a method of protecting a plant by applying an entity or composition as described herein to a plant, the seed material, or the area on which the plant grows.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimisation methods or by biotechnological and recombinant methods or by combinations of these methods, inclusive of the transgenic plants and inclusive of the plant varieties protectable or not protectable by plant breeders' rights. Plant parts are to be understood as meaning all aerial and subterranean plant parts and organs of the plants such as shoot, leaf, flower and root, examples which may be mentioned being leaves, needles, stalks, trunks, flowers, fruiting bodies, fruits, seeds, roots, tubers and rhizomes. The plant parts also include vegetative and generative propagation material, for example cuttings, tubers, rhizomes, seedlings and seeds.

In an aspect, the plant selected from the group consisting of agronomic crops, corn (field, seed & popcorn), sorghum, wheat, barley, rye, oats, rice, forage grasses, soybeans, canola, peanuts, cotton, alfalfa, fruting vegetables (peppers & tomatoes), melons, squash, pumpkins, cucumbers and potatoes.

In an aspect, the plant-parasitic nematode is Reniform nematode, *Rotlyenchulus* spp.; Dagger nematode, *Xiphinema* spp.; Lance nematode, *Hoplolaimus* spp.; Pin nematode, *Paratylenchus* spp.; Ring nematode, *Criconemoides* spp.; Rootknot nematode, *Meloidogyne* spp.; Sheath nematode, *Hemicycliophora* spp.; Spiral nematode, *Helicotylenchus* spp.; Stubbyroot nematode, *Trichodorus* spp.; Cyst nematode, *Heterodera* spp.; Sting nematode, *Belonolaimus*, spp.; and/or Stunt nematode, *Tylenchorhynchus* spp.

In an aspect, the plant is cotton. In an aspect the plant is agronomic crops. In an aspect, the plant is corn (field, seed & popcorn). In an aspect, the plant is sorghum. In an aspect, the plant is wheat. In an aspect, the plant is barley. In an aspect, the plant is rye. In an aspect, the plant is oat. In an aspect, the plant is rice. In an aspect, the plant is forage grasses. In an aspect, the plant is soybeans. In an aspect, the plant is canola. In an aspect, the plant is peanuts. In an aspect, the plant is cotton. In an aspect, the plant is alfalfa. In an aspect, the plant is fruiting vegetables (peppers & tomatoes). In an aspect, the plant is melon. In an aspect, the plant is squash. In an aspect, the plant is pumpkin. In an aspect, the plant is cucumber. In an aspect, the plant is potato.

The following examples serve to illustrate certain aspects of the disclosure and are not intended to limit the disclosure.

Examples

In Vitro Tests Against *R. reniformis*.

An initial test was conducted to evaluate the effect of the metabolites produced by *B. firmus* against second stage juveniles and egg hatching of *R. reniformis*. Eggs of *R. reniformis* were extracted from cotton roots by shaking the root system in a 1% NaOCl solution for four minutes at 120 rpm. The suspension of eggs was collected and rinsed with water through a 25 μm sieve (8). Eggs were rinsed with streptomycin sulfate (300 mg/L) and chlortetracycline (12.5 mg/L) for bacterial disinfection, then with metalaxyl (25 mL/L) and iprodine (20 mL/L) for fungal disinfection, then finally with distilled water. For the second stage juvenile trial, the eggs were placed in a modified Baerman dish on a slide warming tray at 27° C. Second stage juveniles were hatched after three days. To obtain the bacterial metabolite, *Bacillus firmus* GB-126 was grown in 50 mL of Tryptic Soy Broth (TSB) (BACTO™) for four days and then placed in 50 mL plastic tubes and centrifuged for 20 minutes at 4000×g. The supernatant was collected and filtered through a Millipore filter 0.45-0.22 μm to obtain the final bacterial metabolite product (CFE). In vitro trials were conducted on 96-well plates, where volumes of 100 μL of the treatments were transferred to each well, which contained approximately 16 juveniles or 20 eggs of *R. reniformis*. Treatments were i) water control, ii) TSB media control, iii) metabolite 100%, and iv) metabolite 50%. Each treatment had 6 replications, and the entire trial was repeated twice. The number of eggs hatched releasing juveniles was recorded at 0, 24, 48, and 72 hours after inoculation. For the second stage juveniles, number of moving and paralyzed nematodes was recorded at 0, 1, 2, 4, 6, and 12 hours after inoculation. Data were analyzed on SAS 9.1 (SAS Institute Inc.) using the GLIMMIX procedure where the distributional assumption was evaluated with the student panel graphs. Dunnett's option was used to assess the differences with the water and TSB controls.

Table 1 demonstrates the statistical significance of FIG. 1.

TABLE 1

| Treatments | | | Statsical Comparison; P < 0.05 (Hr after Combining) | | |
|---|---|---|---|---|---|
| | | | 24 | 48 | 72 |
| Water Control | vs | CFE 100% | 0.11 | 0.03 | 0.03 |
| Water Control | vs | CFE 50% | 0.11 | 0.04 | 0.03 |
| Media Ctl | vs | CFE 100% | 0.24 | ≤0.001 | ≤0.001 |
| Media Ctl | vs | CFE 50% | 0.28 | ≤0.001 | ≤0.001 |

Figure 2:
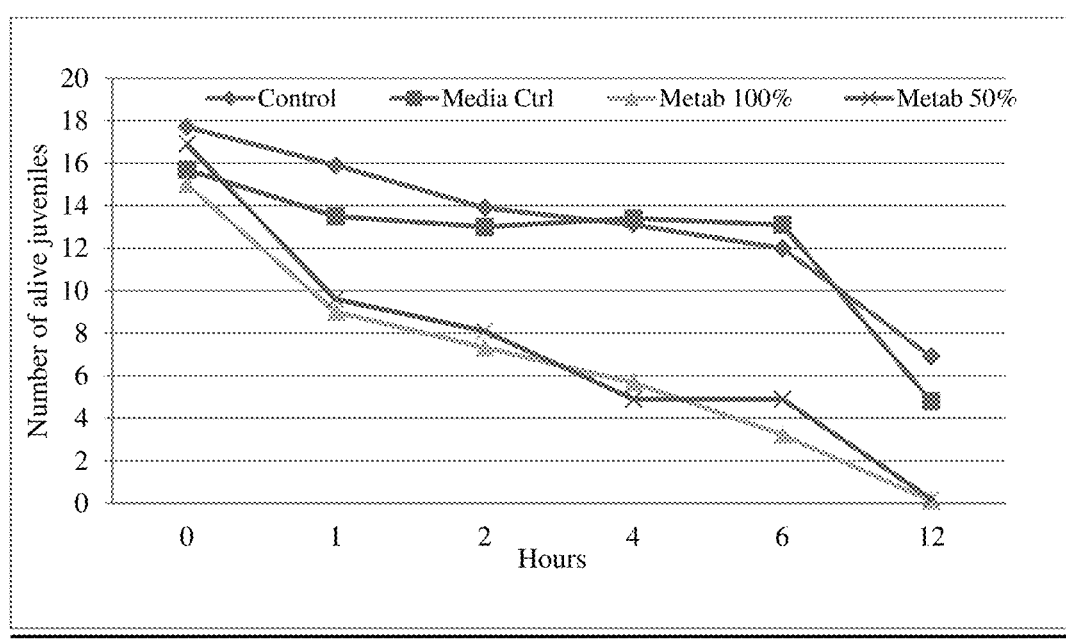
FIG. 2 sets forth the effects of *B. firmus* metabolites at 100% and 50% concentration on *R. reniformis* second stage juveniles as compared to water and media control.
Figure 9:
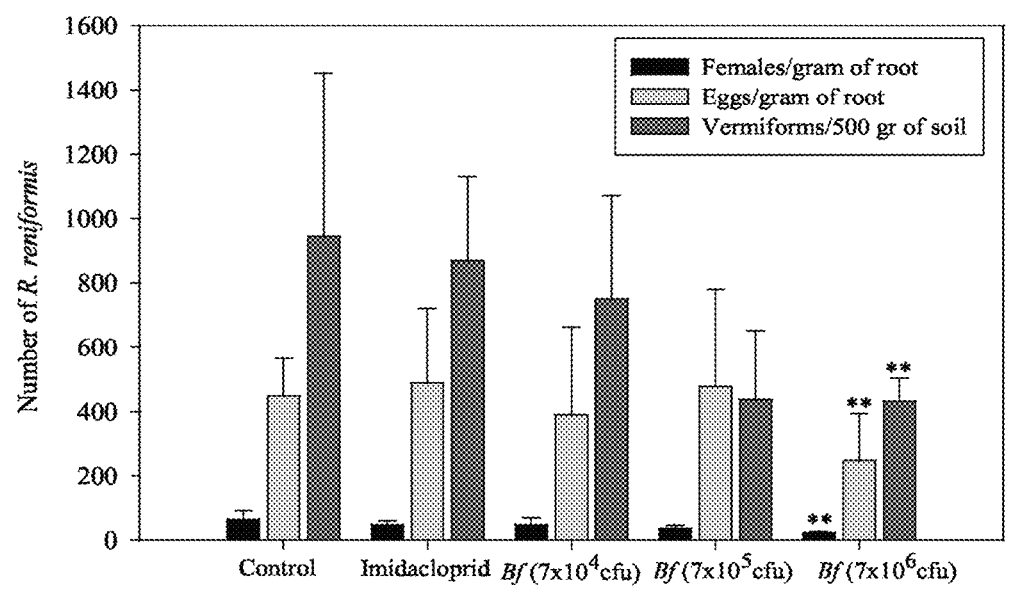
FIG. 9 sets forth *R. reniformis* life stages with cotton seeds treated with *B. firmus* GB-126 at $7 \times 10^6$ cfu/seed under greenhouse conditions in autoclaved soil ($P \leq 0.05$).

Table 2 demonstrates the statistical significant of FIG. 2.

TABLE 2

| Treatments | | | Statsical Comparison; P < 0.05 (Hr after Combining) | | | | |
|---|---|---|---|---|---|---|---|
| | | | 1 | 2 | 4 | 6 | 12 |
| Control | vs | CFE 100% | ≤0.001 | ≤0.001 | ≤0.001 | ≤0.001 | ≤0.001 |
| Control | vs | CFE 50% | ≤0.005 | ≤0.009 | ≤0.001 | ≤0.001 | ≤0.001 |
| Media Ctl | vs | CFE 100% | 0.04 | 0.003 | ≤0.001 | ≤0.001 | 0.02 |
| Media Ctl | vs | CFE 50% | 0.12 | 0.024 | ≤0.001 | ≤0.001 | 0.03 |

Enzyme Characterization of *B. firmus*.

Different enzymatic properties of *B. firmus* GB-126 were evaluated to test their capacity to degrade different media. Production of enzymes was evaluated as positive when a transparent halo was formed around the bacterium culture. *Bacillus firmus* GB-126 was grown for 24 hours on milk agar to test the production of proteases, starch agar for the production of amylases, carboximetil cellulose (CMC) agar for the production of cellulases, chitinase agar for the production of chitinases, and trybutirin agar for the production of lipases. The CMC agar and chitinase agar required the application of 5 ml of congo red to stain the media and a transparent halo after 24 hours of culturing the bacteria. In the case of the starch media, culture was stained with lugol.

Determination of Production of Biosurfactant by *B. firmus*.

Three initial tests were conducted to determine the production of biosurfactant from *B. firmus*. In the first test, the bacterium was grown under blood agar, where a positive production of biosurfactant is indicated by a transparent halo around the bacterial colony. For the second and third tests, *B. firmus* was cultured on nutrient broth at 30° C. for 24 hours. Subsequently, the living cells were recovered by centrifugation at 5,181×g for 15 minutes, and cells were washed twice with NaCl 0.85% (w/v) and later suspended in 5 ml of NaCl 0.85% (w/v). They were used to inoculate 45 ml of saline Davis minimal broth with an inoculum ratio of 1% (v/v). The composition was $K_2HPO_4$ 5.23 g/l, $KH_2PO_4$ 1.91 g/l, $MgSO_4$ 0.09 g/l, $(NH_4)_2SO_4$ 1 g/l, as well as 1 ml/l of trace elements solution ($CoCl_3$ 20 mg/l, $H_3BO_3$ 30 mg/l, $ZnSO_4$ 10 mg/l, $Cu_2SO_4$ 1 mg/l, $Na_2MoO_4$ 3 mg/l, $FeSO_4$ 10 mg/l and $MgSO_4$ 2.6 mg/l). Cultures were incubated at 30° C.±2 at 150 rpm for 3 days. Again *B. firmus* living cells were separated from the supernatant by centrifugation (20 minutes at 4000×g). The supernatant was filtered through a Millipore filter 0.45-0.22 μm to obtain the final bacterial biosurfactant product. This final product was autoclaved twice for 30 minutes at 120° C. at 1 kg/cm³ pressure to kill all the bacterium's living cells and inactivate its enzymes.

In the second test, emulsifying activity of the cell-free supernatant was evaluated by mixing 0.5 ml with 0.5 ml of kerosene and 4 ml of distilled water to a disposable culture tube (borosilicate glass 16×150 mm). The negative control consisted of distilled water and kerosene, and the positive control consisted of distilled water, kerosene, and Triton X-100 (100 mg/ml). Each tube was agitated in a vortex for 1 min and was left to stand for 24 hours. The height of the emulsification ring was then measured in millimeters and compared to that of the chemical emulsifier. If there was positive production of surfactant, the kerosene emulsified it and produced foam. The third test consisted of an oil drop collapse in which one drop of the supernatant was placed on parafilm paper and a drop of oil was placed on top of it. If the drop of oil increased its diameter compared to the media control, the bacteria was considered to have produced a biosurfactant.

Finally, the biosurfactant product was again tested under in vitro conditions in 96 well-plate against second stage juveniles of *R. reniformis*. Volumes of 100 μL of the treatments were transferred to each well, which contained approximately 16 juveniles of *R. reniformis*. Treatments for this trial were i) water control, ii) BPM control, iii) biosurfactant 100%, and iv) *B. firmus* 15×10⁷ cfu/ml. Each treatment was replicated 8 times, and the entire trial was repeated twice. The number of juveniles paralyzed or dead was recorded 30 minutes after inoculation. Data were analyzed on SAS 9.1 (SAS Institute Inc.) as described previously.

Purification and Production of Biosurfactant and In Vitro Evaluations at Different Concentrations Against *R. reniformis*.

For biosurfactant production, *B. firmus* GB-126 was grown aerobically on minimal salt medium containing (per liter) $KH_2PO_4$ (2.0 g), $K_2HPO_4$ (5.0 g), $(NH_4)_2SO_4$ (3.0 g), $NaNO_3$ (2.0 g), NaCl (0.1 g), $MgSO_4$ $H_2O$ (0.2 g), 0 $FeSO_4$ $7H_2O$ (0.01 g), $CaCl_2$ (0.01 g), and 1 ml of a trace element solution. The stock solution of trace elements contained (per liter) $ZnSO_4$ $7H_2O$ (2.32 g), $MnSO_4$ $4H_2O$ (1.78 g), $H_3BO_3$ (0.56 g), $CuSO_4$ $5H_2O$ (1 g), $Na_2MoO_4$ $7H_2O$ (0.39 g), $CoCl_2$ $6H_2O$ (0.42 g), EDTA (1 g), $NiCl_2$ $6H_2O$ (0.004 g), and KI (0.66 g). The medium was supplemented with 0.05% yeast extract (Vater, J. et al.) Glucose was added as a carbon source at a concentration of 2% (wt/vol). The medium pH was 7.1 to 7.2. The organism was grown at 37° C. for 48 h in 2-liter Erlenmeyer flasks containing 800 ml of medium and shaken at 200 rpm in a shaker incubator.

For biosurfactant isolation, bacterial cells were removed from the surfactant-containing medium by centrifugation (13000×g for 15 min at 4° C.). The biosurfactant was precipitated from the supernatant by adding 6 N HCl to obtain a final pH of 2.0. The acid precipitates were recovered by centrifugation (13000×g for 15 min at 4° C.) and were extracted with dichloromethane or methanol (lipopeptide fraction). When methanol was used as the solvent, the extract was neutralized immediately to avoid formation of methyl esters. After precipitation with HCl, the crude fraction dissolved in methanol or dichloromethane was evaporated in a rotary evaporator (Model Buchi R) under a vacuum pump (Model Gem 8890) (Vater, J. et al.). The final purified biosurfactant product was diluted in distilled water at concentrations of 2 ppm, 1 ppm, 0.5 ppm, 0.2 ppm, 0.1 ppm, and 0.02 ppm. These concentrations were evaluated, compared to distilled water control under in vitro conditions on second stage juveniles as described above, with 8 replications per treatment, and repeated twice.

Greenhouse Trials.

To evaluate if *B. firmus* GB-126 induces systemic resistance the following treatments were in tested in a split root system. Treatments consisted of i) water control without nematodes, ii) water control with nematodes, iii) *B. firmus* 1×10⁷ cfu/mL, iv) *B. firmus* 1×10⁶ cfu/mL, or v) *Serratia marcescens* 1×10⁷ cfu/mL. Stoneville 5458 B2RF cotton seeds were germinated in potting mixing soil under greenhouse conditions. Emerging root radicals approximately 2.5 cm in length were split with a razer blade. At 5 days after planting (DAP), soil was removed from the roots and divided into two equal halves. Plants were planted in 960 cm³ pots with each root half in a different cup. At 7 days after splitting the roots, a suspension of 50 mL of treatments was applied on the left side of the root. Five days later, the right side of the root was inoculated with 500 second stage juveniles of *R. reniformis*. The trial was harvested 45 DAP, and plant height, root fresh weight, and number of females and eggs per gram of root were measured. Each treatment had 6 replications and the entire trial was repeated twice.

To evaluate the response of *R. reniformis* to cotton seeds treated with *B. firmus* GB-126, a trial in autoclaved soil was conducted in the Plant Science Research Center (PSRC) of Auburn University. Cotton seeds from cultivar Stoneville 5458 B2RF were treated with *B. firmus* GB126 by the manufacturer in a liquid seed dresser Hegel 1 (Hege Maschinen GmbH, Germany). Presence of the bacterium in the seed was confirmed by culturing the treated seed on Triptic Soy Agar (TSA) adjusted to pH 8.0 and recording the growth after 16 hours. The soil was a Decatur silty clay loam (sand-silt-clay: 17.5-51.3-31.2%; nitrogen: 0.16%; organic matter: 2.2; pH 7.24) from the Tennessee Valley Research and Extension Center (TVREC) near Belle Mina, Ala. The soil was autoclaved using two 90-minute cycles at 130° C. at 15 psi with a 24 hour cool down between cycles. Seed treatments were as follows: i) untreated seed with nematodes; ii) imidacloprid (500 g ai/100 kg) a standard insecticide; iii) *B. firmus* (7×10⁴ cfu/seed) plus imidacloprid (500 g ai/100 kg); iv) *B. firmus* (7×10⁵ cfu/seed) plus imidacloprid (500 g ai/100 kg); and v) *B. firmus* (7×10⁶ cfu/seed) plus imidacloprid (500 g ai/100 kg). The standard insecticide seed treatment imidacloprid was included because this insecticide is commonly applied as a seed treatment and was tested to determine if it has any effect on *B. firmus* or *R. reniformis* life stages.

*Rotlyenchulus reniformis* vermiform life stages were extracted from the soil by modified gravity screening and sucrose centrifugation-flotation. Eggs were extracted from cotton roots by shaking the root system in a 1% NaOCl solution for four minutes at 120 rpm. The nematode suspension was and rinsed with water and collected on a 25 μm sieve. Females in roots were stained with acid fuschin to facilitate enumeration of the females invading the root. Vermiform life stages and eggs were counted under an inverted TS 100 Nikon microscope at 40× magnification. Females embedded in the root systems were quantified at 5× magnification utilizing the Nikon SMZ800 compound microscope. Variables measured were plant height, shoot and root weight, females and eggs per gram of root, and the number of vermiform life stages in 500 cm³ of soil. Greenhouse average temperature where plants were grown was 29° C. Soil moisture was maintained between 40-60% of the maximum water holding capacity. Data were analyzed in SAS 9.1 (SAS Institute Inc.). The distributional assumption was evaluated with the student panel graphs of the GLIMMIX procedure. Dunnett's option was used to assess the differences with the untreated control.

In Vitro and Greenhouse Results

In the first in vitro trial, *R. reniformis* egg hatch was reduced at 48 and 72 hours, when eggs were exposed to *B. firmus* metabolites at 100% and 50%, when compared to the water and media control ($P \leq 0.01$) (FIG. 1). Furthermore, paralysis of second stage juveniles of *R. reniformis* observed within one hour of inoculation in 100% and 50% metabolite through 12 hours when all the second stage juveniles were paralyzed ($P \leq 0.01$) (FIG. 2). No differences were observed between the water and the media controls in these trials ($P \leq 0.99$).

Biosurfactant production was confirmed by the emulsification of kerosene, oil drop collapse, and halo formation in blood agar (FIG. 3). Biosurfactant and living cells of *B. firmus* at a concentration of $15 \times 10^7$ cfu/mL paralyzed all the second stage juveniles within 30 minutes after inoculation when compared to the BP media and water controls ($P \leq 0.01$) (FIG. 3). There were no differences between the two controls ($P \leq 0.99$). Finally, in the last in vitro trial where the pure *B. firmus* biosurfactant was evaluated at different concentrations, the biosurfactant at 2 ppm and 1 ppm paralyzed 100% and 45.9%, of the second stage juveniles of *R. reniformis*, respectively, within 30 minutes (FIG. 4).

These two concentrations produced an increase in paralysis of the second stage juveniles compared to the water control ($P \leq 0.001$). Biosurfactant concentrations of 0.5 ppm, 0.2 ppm, 0.1 ppm, and 0.02 ppm did not paralyze second stage juveniles and were not different from the water control ($P \leq 0.932$). When second stage juveniles from the water control and 2 ppm treatments were observed under SEM, no mechanical damage to the cuticle was observed (FIG. 5A, B). The enzymatic profile of *Bacillus firmus* GB-126 indicated a high enzymatic activity for proteases, amylases, and cellulases forming a transparent halo in milk agar, starch agar, and CMC agar, respectively, within 24 hours. In contrast, no production of chitinases was observed under chitinase agar (FIG. 7).

*Bacillus firmus* GB-126 inhibits the hatch of *R. reniformis* eggs and paralyzes second stage juveniles under in vitro conditions using secondary metabolites from this bacterium and also living cells at a concentration of $15 \times 10^7$ cfu/ml. In greenhouse trials, *B. firmus* GB-126 applied as a seed treatment at a rate of $7 \times 10^6$ cfu/seed reduced number of *R. reniformis* females in the root and juveniles in soil within the first 30 days of planting. The effect of the insecticide imidacloprid, which is used as a seed treatment and formulated with this bacterium, did not show any nematicidal activity.

The results demonstrate that the mode of action of *B. firmus* GB-126 against nematodes is a secondary metabolite toxic to nematodes. This secondary metabolite is a biosurfactant which is responsible for the paralysis of *R. reniformis* juveniles and inhibition of egg hatch under in vitro conditions. *Bacillus firmus* GB-126 biosurfactant needs a minimum concentration of 1 ppm to paralyze second stage juveniles within 30 minutes.

The presence of enzymes (amylases, cellulases, and proteases) suggests the possibility that *B. firmus* GB-126 can have other modes of action against *R. reniformis* and other nematode species during different stages of the life cycle. The production proteases by this bacterium can affect on egg hatching and cause nematode paralysis.

The induction of systemic resistance trial indicated cotton plants treated with *B. firmus* GB-126 ($1 \times 10^6$ cfu/ml) was taller than control with nematodes ($P \leq 0.05$) and *S. marcecens* ($1 \times 10^9$ cfu/ml) treatment ($P \leq 0.01$). There were no differences in left or right root fresh weights or the number of *R. reniformis* females and eggs among the treatments ($P \leq 0.99$) (FIG. 6). In contrast, *B. firmus* GB-126 at a rate of $7 \times 10^6$ cfu/seed reduced the number of females per gram of root ($P \leq 0.001$) and juveniles per 500 cm³ of soil 30 days after planting ($P \leq 0.01$) (FIG. 8). The insecticide imidacloprid did not have any effect on cotton plant growth or *R. reniformis* life stages. Induction of systemic resistance of *B. firmus* GB-126 in cotton plants was not observed at the concentrations evaluated.

In summary, the biocontrol activity of *B. firmus* GB-126 observed in previous trials under greenhouse and field conditions where eggs and juvenile stages were reduced can be explained because the bacterium is producing a biosurfactant that is toxic to the plant-parasitic nematode. No ISR was observed at rates tested. However, *B. firmus* GB-126 possibly has other mechanisms of action against *R. reniformis* due to the presence of proteases that can be deleterious to the nematode.

The invention claimed is:

1. A composition having anti-nematodal activity comprising at least one isolated biosurfactant derived from *Bacillus firmus* and at least one acid precipitate from a culture medium in which the *Bacillus firmus* was grown.

2. The composition according to claim 1, wherein the *Bacillus firmus* is strain GB-126.

3. The composition according to claim 1, wherein the composition has anti-nematodal activity against *Rotlyenchulus reniformis*.

4. The composition according to claim 1, wherein the biosurfactant concentration is greater than 0.5 ppm.

5. The composition according to claim 1, wherein the biosurfactant concentration is at least 1 ppm.

6. The composition according to claim 1, wherein the biosurfactant concentration is from 1 to 2 ppm.

7. The composition according to claim 1, wherein the biosurfactant concentration is at least 2 ppm.

8. The composition according to claim 1, wherein the at least one acid precipitate is obtained by a method comprising:
   (a) adding an acid to the culture medium in which the *Bacillus firmus* has been grown to generate an acid precipitate, and
   (b) isolating the at least one acid precipitate from the culture medium.

9. The composition according to claim 8, wherein the culture medium in which the *Bacillus firmus* has been grown is obtained by growing the *Bacillus firmus* at 37° C. for 48 h in a flask comprising a minimal salt medium supplemented with yeast extract and glucose.

10. The composition according to claim 8, wherein the at least one acid precipitate is generated by adding a mineral acid to the culture medium to obtain a final pH of 2.0.

11. The composition according to claim 10, wherein the mineral acid is HCl.

12. The composition according to claim 8, wherein the at least one acid precipitate is isolated from the culture medium by centrifugation and extracting the at least one acid precipitate with dichloromethane or methanol.

13. The composition according to claim 1, capable of being used to protect a plant.

14. The composition according to claim 1, capable of being used to control at least one plant-parasitic nematode.

15. A method of controlling plant-parasitic nematode comprising applying the composition according to claim 1 to a plant, seed material, and/or an area on which a plant grows.

16. The method according to claim 15, wherein the plant-parasitic nematode is *Rotylenchulus reniformis*.

17. The method according to claim 15, wherein the plant is cotton.

18. A method of protecting a plant comprising applying the composition according to claim 1 to a plant, seed material, and/or an area on which a plant grows.

\* \* \* \* \*